United States Patent [19]

Clegg

[11] Patent Number: 4,607,920
[45] Date of Patent: Aug. 26, 1986

[54] CANADA BALSAM WAFERS

[76] Inventor: John E. Clegg, 2320 Keystone Dr., Orlando, Fla. 32806

[21] Appl. No.: 698,662

[22] Filed: Feb. 6, 1985

[51] Int. Cl.$^4$ .............................. G02B 21/34
[52] U.S. Cl. .................................. 350/536; 427/2
[58] Field of Search ........................ 350/534–536; 427/2; 424/3; 436/176; 156/106, 108

[56] References Cited

U.S. PATENT DOCUMENTS

| 2,351,282 | 6/1944 | Oliver, Jr. | 350/536 |
| 3,031,924 | 5/1962 | Lamal | 350/536 |
| 3,498,860 | 3/1970 | Pickett | 424/3 |
| 3,891,327 | 6/1975 | Welch | 424/3 |
| 4,011,350 | 3/1977 | Markovits et al. | 427/2 |
| 4,120,991 | 10/1978 | Ornstein et al. | 424/3 |

FOREIGN PATENT DOCUMENTS

| 95923 | 7/1980 | Japan | 350/534 |
| 572537 | 10/1945 | United Kingdom | 156/106 |
| 734331 | 7/1955 | United Kingdom | 350/534 |

Primary Examiner—William H. Punter

[57] ABSTRACT

A wafer comprising a thin circular disk of Canada balsam or similar transparent sealing cement of low refractive index for melting and embedding permanent microscopic specimens therein.

1 Claim, 3 Drawing Figures

CANADA BALSAM WAFERS

BACKGROUND

Prior art is limited to Canada balsam in stick form. The stick is held next to a flame, and the balsam melts and flows down over the specimen.

The Canada balsam wafer is placed on top of the specimen in recessed compartments in the slide, and the slide is heated on an electric hot plate. The advantage of using wafers is that the quantity of balsam needed to cover the specimen is predetermined. Also, the use of a hot plate means that many specimens can be sealed during one operation.

DRAWINGS

DESCRIPTION

Figure 1:
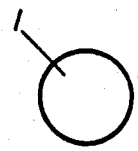
FIG. 1 is a plan view of a Canada balsam wafer.

FIG. 1 is a plan view of a solid Canada balsam wafer 1 with a diameter of 12 mm and a thickness of 1 mm.

Figure 2:
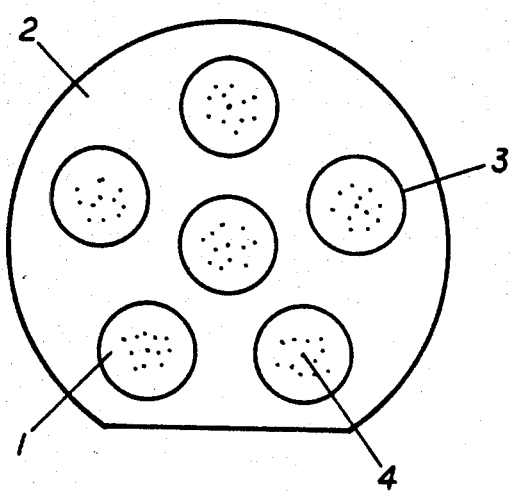
FIG. 2 is a plan view of a granular mineral specimen sealed in Canada balsam in a recessed compartment of a circular specimen slide.
Figure 3:
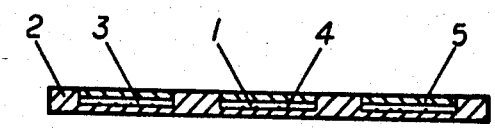
FIG. 3 is a cross section of the circular specimen slide shown in FIG. 2.

FIG. 2 shows a circular specimen slide 2 of heat-resistant glass with six recessed compartments 3 in which crushed mineral specimens 4 were placed. Wafers 1 were placed on top of the specimens 4, and the slide 2 was heated on an electric hot plate, melting wafers 1 and embedding specimens 4 therein. Cover glasses 5 were pressed onto the top of the specimens 4 while the balsam was still molten.

Canada balsam wafers are easy to handle, and the quantity of balsam needed to cover the specimen is predetermined.

I claim:

1. A Canada balsam wafer comprising a thin circular solid disk of Canade balsam, said disk having a prescribed diameter to permit insertion of said disk inside a recessed compartment of a microscopic slide, said disk being of a predetermined volume to cover a mineral specimen embedded therein while molten.

* * * * *